United States Patent
Klapötke et al.

(10) Patent No.: US 10,752,560 B2
(45) Date of Patent: Aug. 25, 2020

(54) 5,5'-BIS(2,4,6-TRINITROPHENYL)-2,2'-BI(1,3,4-OXADIAZOLE) AND BIS(2,4,6-TRINITROBENZOYL) OXALOHYDRAZIDE

(71) Applicant: Ludwig-Maximilians-Universität München, München (DE)

(72) Inventors: Thomas Klapötke, München (DE); Tomasz Grzegorz Witkowski, Hilgertshausen-Tandern (DE)

(73) Assignee: Ludwig-Maximilians-Universitaet Muenchen, Munich (DE)

( * ) Notice: Subject to any disclaimer, the term of this patent is extended or adjusted under 35 U.S.C. 154(b) by 302 days.

(21) Appl. No.: 15/770,124

(22) PCT Filed: Oct. 21, 2016

(86) PCT No.: PCT/EP2016/075400
§ 371 (c)(1),
(2) Date: Apr. 20, 2018

(87) PCT Pub. No.: WO2017/068136
PCT Pub. Date: Apr. 27, 2017

(65) Prior Publication Data
US 2018/0215677 A1    Aug. 2, 2018

(30) Foreign Application Priority Data
Oct. 23, 2015 (EP) ..................... 15191273

(51) Int. Cl.
C06B 25/04    (2006.01)
C06B 25/06    (2006.01)
(Continued)

(52) U.S. Cl.
CPC ............ C06B 25/06 (2013.01); C07C 243/38 (2013.01); C07D 271/10 (2013.01); C07D 413/04 (2013.01)

(58) Field of Classification Search
USPC ...................... 149/88, 92, 105, 106, 109.4
See application file for complete search history.

(56) References Cited

U.S. PATENT DOCUMENTS

| | | | | |
|---|---|---|---|---|
| 4,061,658 A | * | 12/1977 | Dacons | ........... C06B 25/04 549/481 |
| 5,081,255 A | * | 1/1992 | Sitzmann | ........... C07C 219/32 548/145 |
| 2016/0024029 A1 | | 1/2016 | Klapotke et al. | |

FOREIGN PATENT DOCUMENTS

| | | |
|---|---|---|
| JP | 2007-023124 A | 2/2007 |
| WO | 2004/014881 A2 | 2/2004 |

(Continued)

OTHER PUBLICATIONS

International Search Report and Written Opinion, International Application No. PCT/EP2016/075400 (published as WO 2017/068136), dated Dec. 23, 2016 (7 pages).

(Continued)

*Primary Examiner* — James E McDonough
(74) *Attorney, Agent, or Firm* — Prismatic Law Group, PLLC

(57) ABSTRACT

The invention relates to 5,5'-bis(2,4,6-trinitrophenyl)-2,2'-bi(1,3,4-oxadiazole) and bis(2,4,6-trinitrobenzoyl)oxalohydrazide, an energetic active mass comprising or consisting of 5,5'-bis(2,4,6-trinitrophenyl)-2,2'-bi(1,3,4-oxadiazole) and/or bis(2,4,6-trinitrobenzoyl)oxalohydrazide, a use of 5,5'-bis(2,4,6-trinitrophenyl)-2,2'-bi(1,3,4-oxadiazole) as explosive, a use of bis(2,4,6-trinitrobenzoyl)oxalohydrazide as explosive as well as methods for synthesizing 5,5'-bis(2,4,6-trinitrophenyl)-2,2'-bi(1,3,4-oxadiazole) and bis(2,4,6-trinitrobenzoyl)oxalohydrazide.

18 Claims, 1 Drawing Sheet

(51) Int. Cl.
*C07D 271/10* (2006.01)
*C07C 243/38* (2006.01)
*C07D 413/04* (2006.01)
*C06B 25/00* (2006.01)
*C06B 25/34* (2006.01)
*D03D 23/00* (2006.01)
*D03D 43/00* (2006.01)

(56) References Cited

FOREIGN PATENT DOCUMENTS

WO     2014/086599 A1     6/2014
WO     WO-2014086599 A1 *  6/2014   ........... C07D 249/14

OTHER PUBLICATIONS

Kellner et al., "Synthesis, Characterisation and Crystal Structures of Two Bi-oxadiazole Derivatives Featuring the Trifluoromethyl Group," Chem. Eur. J., 21:4238-4241 (2015).
Sitzmann, "2,5-dipicryl-1,3,4-oxadiazole: a shock-sensitive explosive with high thermal stability (thermally-stable substitute for petn)," Journal of Energetic Materials, 6 (1-2):129-144 (1988).

* cited by examiner

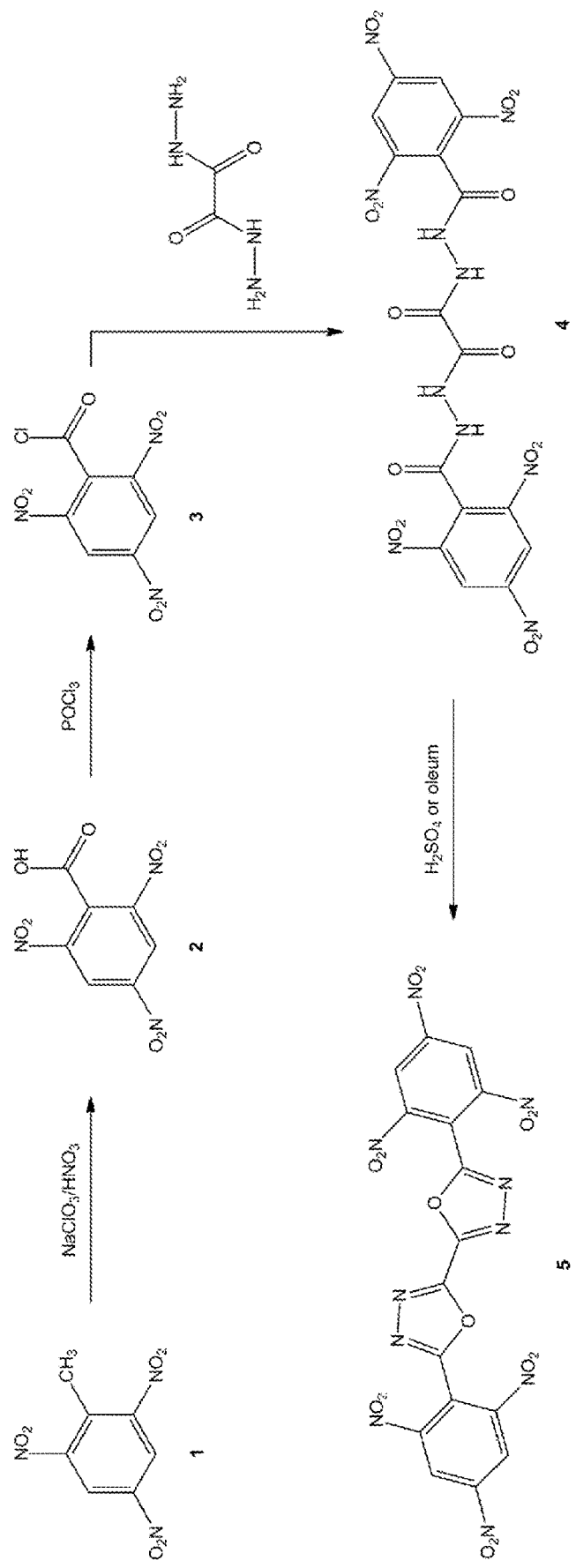

5,5'-BIS(2,4,6-TRINITROPHENYL)-2,2'-BI(1,3,4-OXADIAZOLE) AND BIS(2,4,6-TRINITROBENZOYL) OXALOHYDRAZIDE

The invention relates to 5,5'-bis(2,4,6-trinitrophenyl)-2,2'-bi(1,3,4-oxadiazole) (TKX-55) and its source product bis(2,4,6-trinitrobenzoyl)oxalohydrazide, to an energetic active mass comprising 5,5'-bis(2,4,6-trinitrophenyl)-2,2'-bi(1,3,4-oxadiazole), to a use of 5,5'-bis(2,4,6-trinitrophenyl)-2,2'-bi(1,3,4-oxadiazole) as well as to a method for synthesizing 5,5'-bis(2,4,6-trinitrophenyl)-2,2'-bi(1,3,4-oxadiazole) and bis(2,4,6-trinitrobenzoyl)oxalohydrazide. The lack of thermally stable, i. e. heat resistant, explosives with both tailored performance and tailored volume of gases created during their detonation having low sensitivity to friction, impact and electrostatic discharge is known. There is also a lack of such explosives showing at the same time a low solubility in water, longevity and compatibility as well as an easy and cheap way of synthesis. However, the explosives should not be to insensitive in order to easily undergo detonation upon direct initiation or through a deflagration-to-detonation transition process caused by a priming charge. Thermally stable explosives have received superior consideration because of their capability to resist high temperatures and low pressures such as occurring in deep oil and gas exploitation where thermally stable perforators for oil and gas wells are required, and in space exploration, e. g. for achieving stage separation in space rockets.

Known heat resistant explosives are 2,6-bis(picrylamino)-3,5-dinitropyridine (PYX), 2,2',4,4',6,6'-hexanitrostilbene (HNS) and 1,3,5-triamino-2,4,6-trinitrobenzene (TATB).

From Kettner, M. A., et al., Chem. Eur. J. 2015, 21, 4238-4241 synthesis, characterization and crystal structures of 3,3'-bi-(5-trifluoromethyl-1,2,4-oxadiazole) and 5,5'-bi-(2-trifluoromethyl-1,3,4-oxadiazole) are known. Both substances showed no decomposition until a temperature of 400° C.

Sitzmann, M. E., (1988), Journal of Energetic Materials, 6:1-2, pages 129-144 discloses 2,5-dipicryl-1,3,4-oxadiazole as a shock-sensitive explosive with high thermal stability. The substance is proposed as a substitute for PETN. However, the substance was found to be quite impact sensitive. Impact sensitivity was found to be much higher than that of HNS.

WO 2004/014881 A2 discloses a compound and pharmaceutical formulations containing said compound and a use of said compound in therapy. The compound may consist of a substituted oxadiazole.

From JP 2007023124 A a cellulose compound composition is known. This composition may contain one compound which may comprise two linked oxadiazole groups. The cellulose compound composition is able to form a film having a preferable retardation value as an optical film.

The problem to be solved by the present invention is to provide alternative energetic substances, a precursor of one of these substances, an energetic active mass comprising at least one of these substances, a use of these substance and methods for synthesizing these substances and the precursor of one of these substances.

The problem is solved by the subject-matter of claims 1 to 6 and 12. Embodiments of the invention are subject-matter of claims 7 to 11 and 13 to 15.

According to the invention 5,5'-bis(2,4,6-trinitrophenyl)-2,2'-bi(1,3,4-oxadiazole) (TKX-55) and bis(2,4,6-trinitrobenzoyl)oxalohydrazide are provided. 5,5'-bis(2,4,6-trinitrophenyl)-2,2'-bi(1,3,4-oxadiazole) does not contain acidic protons and is practically insoluble in water. This has positive impact on compatibility with metals used for production of detonators and shaped charges. The synthesis of TKX-55 can be performed using cheap starting materials. TKX-55 can be obtained from these starting materials in high yield and selectivity. Bis(2,4,6-trinitrobenzoyl)oxalohydrazide as well as TKX-55 can be obtained by precipitation from reaction mixtures without involving cost and time consuming processes for their isolation. Synthesis starts with 2,4,6-trinitrotoluene which is also used as a starting material for the currently mostly used heat resistant explosive HNS. All used reagents are produced on industrial scale and are relatively cheap.

Furthermore, the invention concerns an energetic active mass comprising or consisting of TKX-55 and/or bis(2,4,6-trinitrobenzoyl)oxalohydrazide. The invention also concerns a use of TKX-55 as explosive and a use of bis(2,4,6-trinitrobenzoyl)oxalohydrazide as explosive.

An energetic active mass according to the invention is an active mass that deflagrates or detonates after its ignition. The active mass may be a pyrotechnic active mass.

TKX-55 has all the properties with respect to velocity of detonation, detonation pressure, heat of detonation, volume of detonation gases, friction sensitivity, impact sensitivity, electrostatic sensitivity and temperature of decomposition, that are desired for a heat resistant explosive. The thermal stability of TKX-55 is higher than 335° C. The density of the material is 1.837 g·cm$^{-3}$ which is higher than densities of HNS and PYX. This high density results in good performance properties. The detonation velocity is 8.030 m·s$^{-1}$ and the detonation pressure is 273 kbar. Both values are higher than the respective values for HNS and PYX.

The calculation of the detonation velocity as well as the energy of explosion was performed by use of the program EXPLO5, Version 6.02 (M. Sućeska, EXPLO5 V6.02 program, *Brodarski Institute*, Zagreb, Croatia, 2014; M. Sućeska, Calculation of detonation parameters by EXPLO5 computer program, *Materials Science Forum*, 2004, 465-466, 325-330; M. Sućeska, Calculation of the detonation properties of C—H—N—O explosives, *Propellants, Explos., Pyrotech.* 1991, 16, 197-202; M. Sućeska, Evaluation of detonation energy from EXPLO5 computer code results, *Propellants, Explos., Pyrotech.* 1999, 24, 280-285; M. L. Hobbs, M. R. Baer, *Proc. of the 10$^{th}$ Symp. (International) on Detonation*, ONR 33395-12, Boston, Mass., Jul. 12-16, 1993, p. 409).

The features of TKX-55 compared to the features of PYX and HNS are shown in the following table:

|  | PYX | HNS | TKX-55 |
|---|---|---|---|
| Formula | $C_{17}H_7N_{11}O_{16}$ | $C_{14}H_6N_6O_{12}$ | $C_{16}H_4N_{10}O_{14}$ |
| MW [g · mol$^{-1}$] | 621.34 | 450.23 | 560.26 |
| IS $^{a)}$ [J] | 10 | 5 | 5 |
| FS $^{b)}$ [N] | 360 | 240 | >360 |
| ESD $^{c)}$ [J] | 0.5 | 0.8 | 1.0 |
| N $^{d)}$ [%] | 24.80 | 18.67 | 25.00 |
| Ω $^{e)}$ [%] | −55.36 | −67.6 | −57.11 |
| $T_{dec}$ $^{f)}$ [° C.] | 356 | >320 | >335 |
| ρ $^{g)}$ [g · cm$^{-3}$] | 1.757 | 1.74 | 1.837 |
| $\Delta_f H°$ [kJ · mol$^{-1}$] | 43.7 | 78.2 | 197.6 |
| EXPLO5 V6.02 | | | |
| −$\Delta_E U°$ $^{i)}$ [kJ · kg$^{-1}$] | 4870 | 5142 | 4961 |
| $T_E$ $^{j)}$ [K] | 3609 | 3677 | 3681 |

-continued

|  | PYX | HNS | TKX-55 |
|---|---|---|---|
| $P_{C-J}{}^{k)}$ [kbar] | 251 | 243 | 273 |
| $V_{Det}{}^{l)}$ [m·s$^{-1}$] | 7757 | 7612 | 8030 |
| Gas vol. $^{m)}$ [dm$^3$·kg$^{-1}$] | 633 | 602 | 604 |

$^{a)}$ Impact sensitivity (BAM drophammer);
$^{b)}$ Friction sensitivity (BAM friction tester);
$^{c)}$ Electrostatic discharge device (OZM research);
$^{d)}$ Nitrogen content;
$^{e)}$ Oxygen balance;
$^{f)}$ Temperature of decomposition (DSC, β = 5 [° C.]);
$^{g)}$ Density at 298 K;
$^{h)}$ Standard molar enthalpy of formation (calculated, CBS-4M method);
$^{i)}$ Heat of detonation;
$^{j)}$ Detonation temperature;
$^{k)}$ Detonation pressure;
$^{l)}$ Detonation velocity;
$^{m)}$ Volume of detonation gases at standard temperature and pressure conditions (assuming only gaseous products).

For the calculation of the energy of formation according to the table the enthalpies (H) and free energies (G) were calculated using the complete basis set (CBS) method of Petersson and coworkers in order to obtain very accurate energies. The CBS models use the known asymptotic convergence of pair natural orbital expressions to extrapolate from calculations using a finite basis set to the estimated complete basis set limit. CBS-4 begins with a HF/3-21G(d) geometry optimization; the zero point energy is computed at the same level. It then uses a large basis set SCF calculation as a base energy, and a MP2/6-31+G calculation with a CBS extrapolation to correct the energy through second order. A MP4(SDQ)/6-31+(d,p) calculation is used to approximate higher order contributions. For the calculation of the energies of formation according to the table the modified CBS-4M method (M referring to the use of minimal population localization) was applied. The CBS-4M method is a re-parameterized version of the original CBS-4 method and also includes some additional empirical corrections.

DSC measurements at a heating rate of 5° C.·min$^{-1}$ revealed that TKX-55 is thermally stable up to a temperature of more than 335° C. Based on gas pycnometer measurements at room-temperature the density of the material was determined to be 1.837 g·cm$^{-3}$ at a temperature of 298 K. This density provides the material with a good energetic performance. As can be seen from the table the detonation parameters of TKX-55 are superior and its sensitivity is low. The combination of these values make TKX-55 a superior heat resistant explosive. A comparison with HNS shows that TKX-55 has a decomposition point which is higher by 15° C. and that TKX-55 is a higher performing explosive.

DSC measurements at a heating rate of 5° C.·min$^{-1}$ revealed a temperature of decomposition of 307° C. for bis(2,4,6-trinitrobenzoyl)oxalohydrazide. Therefore, bis(2,4,6-trinitrobenzoyl)oxalohydrazide can also be considered as thermally stable explosive.

TKX-55 can be obtained by dehydration of its precursor bis(2,4,6-trinitroben-zoyl)oxalohydrazide which is also a thermally stable molecule.

The invention also concerns a method of synthesizing TKX-55, wherein bis(2,4,6-trinitrobenzoyl)oxalohydrazide is dehydrated in a solution to give said TKX-55. Bis(2,4,6-trinitrobenzoyl)oxalohydrazide can be dehydrated by contacting bis(2,4,6-trinitrobenzoyl)oxalohydrazide with a dehydration agent. The dehydration agent may consist of or comprise at least one agent selected from H$_2$SO$_4$, oleum, p-tosyl chloride, polyphosphoric acid, phosphorus pentoxide, acetic anhydride, phosphorus oxychloride, sulfur trioxide, methyl N-(triethylammoniumsulfonyl)carbamate (Burgess reagent, CAS: 29684-56-8), trifluoroacetic acid (TFA=CF$_3$CO$_2$H), and a mixture of methanesulfonic acid and phosphorus pentoxide, in particular selected from H$_2$SO$_4$ and oleum.

The solution may comprise H$_2$O or another polar solvent. The bis(2,4,6-trinitrobenzoyl)oxalohydrazide can be dehydrated at a temperature of up to 40° C., in particular 15° C. to 40° C., in particular 18° C. to 35° C., in particular 20° C. to 30° C.

The TKX-55 can be obtained from the solution by precipitation by reducing the temperature of the solution below 35° C., in particular below 15° C., in particular below 10° C., in particular below 8° C., in particular below 6° C., in particular below 4° C., in particular below 2° C., in particular below 1° C. The precipitate can be washed with water until it is acid free and subsequently dried.

The invention also concerns a method for synthesizing bis(2,4,6-trinitroben-zoyl)oxalohydrazide, wherein 2,4,6-trinitrobenzoyl chloride is reacted with oxalyldihydrazide in an aprotic solvent. The aprotic solvent may be tetrahydrofuran (THF), benzene or another solvent in which 2,4,6-trinitrobenzoyl chloride is soluble or a mixture of at least two of these solvents.

The 2,4,6-trinitrobenzoyl chloride can be reacted with the oxalyldihydrazide at a temperature above the melting point of the aprotic solvent, in particular at a temperature of 15° C. to 40° C., in particular 18° C. to 35° C., in particular 20° C. to 30° C.

The bis(2,4,6-trinitrobenzoyl)oxalohydrazide can be obtained from the solvent by precipitation that occurs at the reaction temperature. For the precipitation it is not required to reduce the temperature of the solvent. The precipitated bis(2,4,6-trinitrobenzoyl)oxalohydrazide can be washed with the aprotic solvent followed by washing with diethyl ether and drying.

The synthesis of TKX-55 can be performed in four steps as shown in FIG. 1. The first step is an oxidation of 2,4,6-trinitrotoluene using the mixture system of NaClO$_3$/HNO$_3$. The second step involves chlorination of 2,4,6-trinitrobenzoic acid using POCl$_3$, pyridine/POCl$_3$ or SOCl$_2$/CH$_2$Cl$_2$. The obtained 2,4,6-trinitrobenzoyl chloride does not react with water and is insoluble in water. It is reacted in a third step with oxalyldihydrazide. Oxalyldihydrazide can be cheaply and practically quantitatively obtained via reaction of diethyl oxalate with hydrazinium. In a last step the resulting bis(2,4,6-trinitrobenzoyl)oxalohydrazide is added to concentrated H$_2$SO$_4$ or oleum and stirred at room temperature followed by pouring of the reaction mixture onto crashed ice yielding TKX-55.

EMBODIMENTS OF THE INVENTION

A) Synthesis of bis(2,4,6-trinitrobenzoyl)oxalohydrazide

To a solution of 2,4,6-trinitrobenzoyl chloride (10 mmol, 2.76 g) in 25 mL of tetrahydrofuran (THF) oxalyldihydrazide (5 mmol, 0.59 g) was added in one portion. The mixture was stirred for 24 hours at ambient temperature. The precipitate was filtered and washed with THF and diethyl ether (yield 83%, 2.48 g).

The features of the product are as follows:

DSC (5° C.·min$^{-1}$): 307° C. (dec.); $^1$H NMR (400.18 MHz, DMSO-d$_6$, 26° C., ppm) δ: 11.47 (s, 2H, NH), 11.42 (s, 2H, NH); 9.13 (s, 4H, CH); $^{13}$C{$^1$H} NMR (100.0 MHz, DMSO-d$_6$, 26° C., ppm) δ: 158.0, 157.5, 147.92, 147.91, 129.2, 124.1; MS (DEI+): ml z=596.1 [M]$^+$; IR (ATR, cm$^{-1}$) ṽ: 3339 (m), 3295 (m), 3108 (w), 1714 (vs), 1671 (s), 1606 (m), 1552 (s), 1536 (vs), 1484 (m), 1452 (w), 1344 (vs), 1293 (m), 1230 (m), 1181 (w), 1076 (w), 923 (s), 830 (w), 819 (w), 784 (w), 736 (s), 725 (s), 686 (m); EA ($C_{16}H_8N_{10}O_{16}$, 596.29): calc.: C, 32.23; H, 1.35; N, 23.49%; found C, 32.22; H, 1.61; N, 22.87%.

B) Synthesis of TKX-55

To fuming sulfuric acid (20%, 10 mL) bis(2,4,6-trinitrobenzoyl)oxalohydrazide (1 mmol, 0.60 g) was added. The mixture was stirred for 24 hours at ambient temperature and poured onto crushed ice. The precipitate was filtered, washed with water until acid free and dried (yield 93%, 0.52 g).

The features of the product are as follows:

DSC (5° C.·min$^{-1}$): >335° C. (dec.); $^1$H NMR (399.78 MHz, DMSO-$d_6$, 22° C., ppm) δ: 9.40 (s, 4H, CH); $^{13}$C{$^1$H} NMR (100.5 MHz, DMSO-$d_6$, 24° C., ppm) δ: 158.1, 154.0, 150.3, 149.4, 125.3, 116.8; MS (DEI+): ml z=561.1 [M+1]$^+$; IR (ATR, 25° C., cm$^{-1}$) ṽ: 3089 (w), 1608 (m), 1541 (s), 1468 (w), 1403 (w), 1341 (s), 1187 (w), 1152 (m), 1064 (m), 993 (w), 966 (w), 955 (w), 923 (s), 925 (w), 780 (w), 759 (m), 740 (m), 722 (s), 694 (w), 673 (w); Raman (1064 nm, 300 mW, 25° C., cm$^{-1}$) ṽ: 1639 (100), 1565 (32), 1360 (66), 1026 (29), 977 (11), 967 (12), 924 (7), 825 (18); EA ($C_{16}H_4N_{10}O_{14}$, 560.26): calc.: C, 34.30; H, 0.72; N, 25.00%; found C, 34.33; H, 1.01; N, 25.01%; BAM drophammer: 5 J; friction tester: >360 N; ESD: 1.0 J.

In the above features of bis(2,4,6-trinitrobenzoyl)oxalohydrazide and TKX-55 EA means "elementary analysis", wherein "calc." means the calculated and "found" means the actually determined percentage by weight of the respective elements. MS (DEI+) means the result obtained by mass spectrometry using Desorption Electron Ionisation. The result is given as mass (m) per charge (z), i. e. the mass (in atomic mass units) of the molecule having a single positive charge.

The invention claimed is:

1. Compound selected from the group consisting of 5,5'-bis(2,4,6-trinitrophenyl)-2,2'-bi(1,3,4-oxadiazole) and bis(2,4,6-trinitrobenzoyl)oxalohydrazide.

2. Energetic active mass comprising or consisting of 5,5'-bis(2,4,6-trinitrophenyl)-2,2'-bi(1,3,4-oxadiazole) and/or bis(2,4,6-trinitrobenzoyl)oxalohydrazide.

3. Method of using the compound of claim 1 as explosive.

4. Method for synthesizing the compound of claim 1, wherein the compound is 5,5'-bis(2,4,6-trinitrophenyl)-2,2'-bi(1,3,4-oxadiazole), wherein bis(2,4,6-trinitrobenzoyl)oxalohydrazide is dehydrated in a solution to give said 5,5'-bis(2,4,6- trinitrophenyl)-2,2'-bi(1,3,4-oxadiazole).

5. Method according to claim 4, wherein said bis(2,4,6-trinitrobenzoyl)oxalohydrazide is dehydrated by contacting bis(2,4,6-trinitrobenzoyl)oxalohydrazide with a dehydration agent.

6. Method according to claim 5, wherein the dehydration agent consists of or comprises at least one agent selected from $H_2SO_4$, oleum, p-tosyl chloride, polyphosphoric acid, phosphorus pentoxide, acetic anhydride, phosphorus oxychloride, sulfur trioxide, methyl N-(triethylammoniumsulfonyl)carbamate, trifluoroacetic acid, and a mixture of methanesulfonic acid and phosphorus pentoxide.

7. Method according to claim 4, wherein the solution comprises $H_2O$ or another polar solvent.

8. Method according to claim 4, wherein said bis(2,4,6-trinitrobenzoyl)oxalohydrazide is dehydrated at a temperature of up to 40° C.

9. Method according to claim 4, wherein the 5,5'-bis(2,4,6-trinitrophenyl)-2,2'-bi(1,3,4-oxadiazole) is obtained from the solution by precipitation by reducing the temperature of the solution below 35° C.

10. Method for synthesizing the compound of claim 1, wherein the compound is bis(2,4,6-trinitrobenzoyl)oxalohydrazide, wherein 2,4,6-trinitrobenzoyl chloride is reacted with oxalyldihydrazide in an aprotic solvent.

11. Method according to claim 10, wherein the aprotic solvent comprises or consists of tetrahydrofuran (THF) and/or benzene.

12. Method according to claim 10, wherein said 2,4,6-trinitrobenzoyl chloride is reacted with said oxalyldihydrazide at a temperature of 15° C. to 40° C.

13. Method according to claim 10, wherein said bis(2,4,6-trinitrobenzoyl)oxalohydrazide is obtained from the aprotic solvent by precipitation.

14. Compound according to claim 1, wherein the compound is 5,5'-bis(2,4,6-trinitrophenyl)-2,2'-bi(1,3,4-oxadiazole).

15. Compound according to claim 1, wherein the compound is bis(2,4,6-trinitrobenzoyl)oxalohydrazide.

16. Energetic active mass according to claim 2, wherein the energetic active mass comprises or consists of 5,5'-bis(2,4,6-trinitrophenyl)-2,2'-bi(1,3,4-oxadiazole).

17. Energetic active mass according to claim 2, wherein the energetic active mass comprises or consists of bis(2,4,6-trinitrobenzoyl)oxalohydrazide.

18. Energetic active mass according to claim 2, wherein the energetic active mass comprises or consists of 5,5'-bis(2,4,6-trinitrophenyl)-2,2'-bi(1,3,4-oxadiazole) and bis(2,4,6-trinitrobenzoyl)oxalohydrazide.

* * * * *